US012343025B2

(12) United States Patent
Hinding et al.

(10) Patent No.: US 12,343,025 B2
(45) Date of Patent: Jul. 1, 2025

(54) METHOD FOR DETERMINING AN OPTIMAL FREQUENCY OF AN OSCILLATING MOVEMENT OF A FORCE-ACCELERATED PROJECTILE OF AN INTRACORPOREAL LITHOTRIPSY APPARATUS

(71) Applicant: KARL STORZ SE & Co. KG, Tuttlingen (DE)

(72) Inventors: Thomas Hinding, Tuttlingen (DE); Bernhard Glöggler, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 399 days.

(21) Appl. No.: 18/013,354

(22) PCT Filed: Jun. 29, 2021

(86) PCT No.: PCT/EP2021/067828
§ 371 (c)(1),
(2) Date: Dec. 28, 2022

(87) PCT Pub. No.: WO2022/002926
PCT Pub. Date: Jan. 6, 2022

(65) Prior Publication Data
US 2023/0293194 A1    Sep. 21, 2023

(30) Foreign Application Priority Data
Jul. 1, 2020 (DE) .................... 10 2020 117 364.4

(51) Int. Cl.
*A61B 17/22* (2006.01)
*A61B 17/00* (2006.01)
(52) U.S. Cl.
CPC . *A61B 17/22012* (2013.01); *A61B 2017/0011* (2013.01); *A61B 2017/22014* (2013.01)

(58) Field of Classification Search
CPC .... A61B 17/22012; A61B 2017/22014; A61B 2017/0011
See application file for complete search history.

(56) References Cited

U.S. PATENT DOCUMENTS 6,214,017 B1 * 4/2001 Stoddard ........ A61B 17/320068
606/128
9,642,640 B2 * 5/2017 Faherty ............ A61B 17/22004
(Continued)

FOREIGN PATENT DOCUMENTS

| DE | 102018101215 A1 | 7/2019 |
| EP | 1163882 A1 | 12/2001 |
| EP | 1163883 A1 | 12/2001 |

OTHER PUBLICATIONS

Oct. 15, 2021—(WO) International Search Report & Written Opinion—App. No. PCT/EP2021/067828.
Oct. 16, 2024—(EP) Examination Report—App. No. EP21742053.8.

*Primary Examiner* — Phong Son H Dang
(74) *Attorney, Agent, or Firm* — Banner & Witcoff, Ltd.

(57) ABSTRACT

The invention relates to a method for determining an optimal frequency of an oscillating movement of a force-accelerated projectile of an intracorporeal pneumatic lithotripsy apparatus, including the following steps: repeatedly accelerating the projectile from a first proximal stop of an acceleration path to a second distal stop, and from the second stop to the first stop, wherein a piezo element is arranged between a proximally arranged counter bearing and a distally arranged horn and is mechanically coupled to the counter bearing and to the horn, and the horn has a distally arranged sonotrode, wherein the acceleration path is arranged in the interior of the counter bearing and of the horn and the first stop is arranged at a distal end of the counter bearing and the second stop is arranged at a distal end of the horn, detecting an
(Continued)

Figure 1:
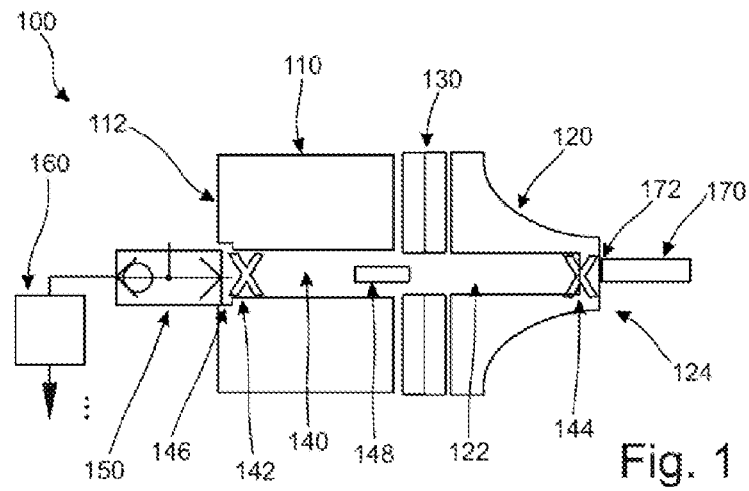

electrical signal from the piezo element caused by a tremor at the first stop and/or the second stop as a result of the projectile; and using the detected electrical signal to control a medium which generates the force and which is used to accelerate the projectile from the first stop of the acceleration path to the second stop, and from the second stop to the first stop.

9 Claims, 2 Drawing Sheets

(56) References Cited

U.S. PATENT DOCUMENTS

| | | |
|---|---|---|
| 10,285,773 B2 * | 5/2019 | Faherty ................ A61B 17/225 |
| 11,109,874 B2 * | 9/2021 | Gavala ............. A61B 17/32002 |
| 2002/0010486 A1 * | 1/2002 | Hirt ................. A61B 17/22012 |
| | | 606/169 |

* cited by examiner

METHOD FOR DETERMINING AN OPTIMAL FREQUENCY OF AN OSCILLATING MOVEMENT OF A FORCE-ACCELERATED PROJECTILE OF AN INTRACORPOREAL LITHOTRIPSY APPARATUS

CROSS-REFERENCE TO RELATED APPLICATIONS

The present application claims priority from and is a U.S. National Phase of International Application No. PCT/EP2021/067828, which was filed on Jun. 29, 2021, designating the United States of America and claiming priority to German Patent Application No. DE 10 2020 117 364.4, filed on Jul. 1, 2020. This application claims priority to and the benefit of the above-identified applications, which are all fully incorporated by reference herein in their entireties.

The invention relates to a method for determining an optimal frequency of an oscillating movement of a force-accelerated projectile of an intracorporeal lithotripsy apparatus and a corresponding lithotripsy apparatus.

Lithotripsy is a method known in the state of the art for disintegrating stones, which are also called concrements, in the urinary tracts, the kidneys and/or the bladder. Most lithotripsy devices use ultrasound, laser or pneumatic energy sources to disintegrate such stones.

A lithotripter known in the state of the art contains a shaft, which is connected to an electrically controlled driver or to a pneumatic actuator. The shaft is inserted into the anatomy of the patient at a point close to the stone and a waveform is sent through the shaft to break up the stone with the shaft and to generate a pneumatic hammer or bore effect on the stone, whereby the stone is fragmented into smaller, easier-to-remove elements, which can then be removed by means of a suction-flushing pump. This is a method of intracorporeal lithotripsy.

In order to be able to design the stone disintegration as effectively as possible, —the combination of two systems is known, for example the methods using ultrasound and pneumatically-generated mechanical impact.

It is also known that the ultrasound and the pneumatic system can be operated independently or together. If they are operated together and the pneumatic, driven projectile impacts the sonotrode, this results in interference with the ultrasound generator. If the projectile impacts the sonotrode, the impact also affects a piezo element generating the ultrasonic waves such that a voltage is induced in the generator.

In the case of certain lithotripsy systems, due to this interference, the control can no longer be maintained, at which point an error message is displayed and the system needs to be restarted.

It is known that in the case of the pneumatic system, impacts that are as high in energy as possible should be achieved with a frequency that is as high or as optimal as possible. It is also known that the pressure, the mass and the acceleration path significantly influence the energy which is emitted when the projectile impacts the sonotrode.

An object of the present invention is to improve the state of the art. It is in particular an object of the invention to indicate a combined lithotripter-ultrasound-pneumatic system that functions without interference. It is for example a further object of the invention to indicate such a combined system, which maximises a disintegration force of a projectile used in the pneumatic system. It is in particular a further object of the invention to indicate such a combined system, which maximises a frequency of a repeated acceleration of a used projectile.

This object is achieved by means of a method for determining an optimal frequency of an oscillating movement of a force-accelerated projectile having the features of independent claim 1. Advantageous further developments of the invention are indicated in the dependent claims.

The following terminology will first be explained:

The present method for determining an optimal frequency of an oscillating movement of a force-accelerated projectile of an intracorporeal lithotripsy apparatus, in particular a lithotripsy apparatus, can also be understood, among other things, as a method for testing, calibrating, adjusting or optimising the functionality of the lithotripsy apparatus. In particular, the method is not carried out during a surgical intervention. The method is e.g. carried out at the factory or before or accordingly after a surgical intervention.

The terminology 'an optimal frequency of the oscillating movement of a force-accelerated projectile in intracorporeal, in particular pneumatic, lithotripsy' can be understood in the present case as a maximum frequency. Even though the frequency is "only" optimised, an optimal frequency is mentioned in the present case.

In the case of the present lithotripsy, a projectile running within a closed space is accelerated from a first end of the space to a second end of the space such that the projectile is braked at the second end. The rapid braking of the projectile releases impact energy, which is transmitted via the projectile outwards to the horn and the sonotrode fastened thereto. After the projectile has been braked, said projectile is preferably transported back from the second end to the first end, at which point the projectile can again be accelerated in the other direction. The repeated movement of the projectile from the first end to the second end and back again is designated in the present case as an oscillating movement.

Direct contact of the tip of the sonotrode with the concrement to be disintegrated is decisive for the transmission of the impact energy.

The piezo element is preferably operated in resonance with the horn and the sonotrode to generate ultrasonic waves.

The lithotripsy apparatus is an apparatus for carrying out lithotripsy, in particular a handheld device with an endoscope.

The ultrasonic frequency of the piezo element is preferably at 27 kHz. The ultrasonic signal is preferably generated with a signal generator.

The acceleration path is a separate spatial region in the present case in which the projectile can be accelerated from one end to the other end. The projectile can slide back and forth within this spatial region freely and preferably with little friction.

The acceleration path preferably extends partially in the horn. The end of the acceleration path is preferably coupled to the sonotrode at the second stop.

The counter bearing is preferably a reflector for ultrasonic waves. The horn is used to relay the ultrasonic waves generated by the piezo element to the sonotrode used as the waveguide. At the same time however, counter bearing and horn serve as a mechanical holder for the acceleration path, which is arranged in the interior of the reflector and of the horn.

The counter bearing and/or the horn have in particular a hollow-cylindrical shape.

When the accelerated projectile is braked at the first or second stop, a tremor occurs, which also shakes the piezo element as a result of the mechanical coupling. Due to the piezoelectric effect, this tremor causes a voltage, which is induced at the ends of the piezo element and which can be detected by means of an electronic circuit. When the projectile impacts, a high voltage is generated in the piezo element, which disrupts the resonance frequency of the ultrasonic generator. The electronics present therein must readjust in order to come back into resonance. This readjustment can be used as a signal to determine the position of the projectile.

A core idea of the invention is to use information, which can be identified from this electrical signal, for example the time or the times of occurrence of the induced voltage, to regulate the timed actuation of a medium accelerating the projectile, such that a force transmitted from the projectile to a concrement to be disintegrated is at the maximum and/or the frequency of the oscillation of the projectile in the interior of the acceleration path is maximised and/or optimised.

Another core idea of the invention is in particular to also use the piezo element, which is used to generate the ultrasonic waves, as a sensor in order to optimise the movement of the projectile in the interior of the acceleration path.

The projectile can be accelerated by means of compressed air, by means of an electromagnetically imparted force or by means of a mechanical apparatus. The medium which generates the force can be compressed air, an electromagnetic field or a mechanical apparatus. The term 'medium' is used in the present case in the sense of "a means, which transmits a force from a first thing to a second thing". The term "medium which generates the force" can be understood in the present case as any device, any material or any physical field or force in the above sense. An apparatus for accelerating the projectile can for example be a rail gun. Alternatively or additionally, mechanical apparatuses can for example be used to accelerate the projectile.

The piezo element can be excited with an ultrasonic frequency. To this end, the piezo element is preferably connected to a signal generator, which generates an ultrasonic frequency.

The acceleration path can be implemented with a pipe section, wherein a first end of the pipe section has the first stop and a second end of the pipe section has the second stop. The pipe section is preferably a hollow-cylindrical shape.

A first valve can be used to introduce compressed air into the pipe section such that the projectile is accelerated from the first stop to the second stop. In particular, a compressed air source is connected to the first stop, i.e. to the first end of the pipe section, by means of a check valve. Furthermore, the air displaced by the projectile can be buffered in a storage chamber, which is separate from the acceleration path and/or the pipe section. This buffering is preferably temporary. After the first valve has closed, the buffered compressed air can be used to accelerate the projectile from the second stop to the first stop.

A pressure of between 0.5 bar and 5 bar can be used for the compressed air.

In particular, a second valve, which is arranged between the pipe section and/or the acceleration path and the storage chamber, is automatically opened, after the first valve has been closed, in order to accelerate the projectile from the second stop to the first stop.

The first valve closes in particular after the projectile has reached the second stop.

The electrical signal of the piezo element can be a power signal, which can be measured by means of a coil. In this manner, the electrical signal can be effectively detected with low losses from the circuit included in the piezo element. The principle of a current clamp can be used here.

In accordance with the method according to the invention, the power signal measured at the piezo element can also be frequency-filtered in order to keep the frequency range, at which the frequency is located when the piezo element is operated, away from the circuit, in which the measured power signal is further processed. Such a filter could for example be an RC, RL or an RLC circuit.

The frequency-filtered power signal is in particular rectified in order to obtain an analogue signal.

To this end, a rectifier or a type of rectifier can be used. For example, a buffer circuit is used.

Furthermore, at least one threshold value of the rectified frequency-filtered power signal can be identified, which corresponds to the projectile reaching the first or second stop. In this way, depending on the current strength, which the projectile generates when impacting the piezo element, it can be decided whether it has impacted the first proximal stop or the second distal stop. The time, at which the corresponding stop takes place, can preferably also be identified from the signal. The location information "distal" is understood in the present case as a point on a medical device, which is remote from the user or operator. The location information "proximal" is understood in the present case as a point on a medical device, which is close to a user or operator.

A microcontroller can be used to evaluate the rectified, frequency-filtered power signal and to evaluate the identified threshold values. The microcontroller can carry out plausibility tests here in order to minimise incorrect measurements or measurement errors or exclude them accordingly.

The method can be carried out by means of regulation such that the voltage swing caused by the tremor or impact of the projectile at the first stop is regulated to a predefined value. The predefined value can be the smallest value which is different from zero and which can be resolved using the present electronics. The regulation can for example be a two-point regulation, in which the predefined value is the target value and the actual value is moved around the target value. The regulation causes, in particular depending on the actual value, an earlier or later actuation of a second valve, which can release compressed air buffered in a storage chamber, such that the projectile is accelerated from the second stop to the first stop.

In a further aspect, the invention is achieved by means of a lithotripsy apparatus. The lithotripsy apparatus is suited in particular for carrying out the method described above.

The lithotripsy apparatus has a piezo element arranged between a proximally arranged counter bearing and a distally arranged horn, wherein the piezo element is mechanically coupled to the counter bearing and to the horn. In this case, a hollow-cylindrical acceleration path is arranged in the interior of the counter bearing and the horn, and has, at a proximal end of the counter bearing, a first stop and, at a distal end of the horn, has a second stop.

The proximal end of the acceleration path has in particular a compressed air source connected by means of a first valve.

A projectile is in particular arranged in the interior of the acceleration path, said projectile being designed and configured to be accelerated by means of compressed air of the compressed air source from the first stop to the second stop and to be accelerated by means of compressed air displaced by the projectile and buffered in a storage chamber from the second stop to the first stop. A second valve can be arranged between the storage chamber and the acceleration path.

A sonotrode designed as a waveguide is arranged in particular at a distal end of the horn.

In this case, a proximal end of the sonotrode is mechanically coupled to the second stop of the acceleration path.

The lithotripsy apparatus is designed and configured in this case in particular such that an electrical signal of the piezo element caused by a tremor at the first and/or second stop as a result of the projectile can be detected and is used to regulate the compressed air of the compressed air source.

Figure 2:
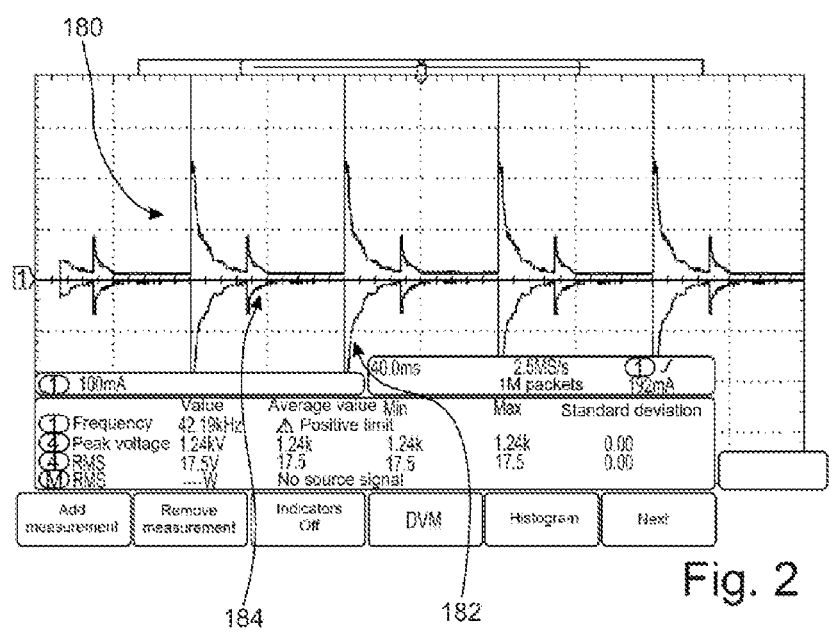

The invention will be explained in more detail below on the basis of an exemplary embodiment, wherein FIG. 1 shows a schematic illustration of a lithotripsy apparatus according to an embodiment of the invention and FIG. 2 shows a measurement of an electrical power signal applied to a piezo element against the time during which a method is carried out according to an embodiment of the invention.

Figure 3:
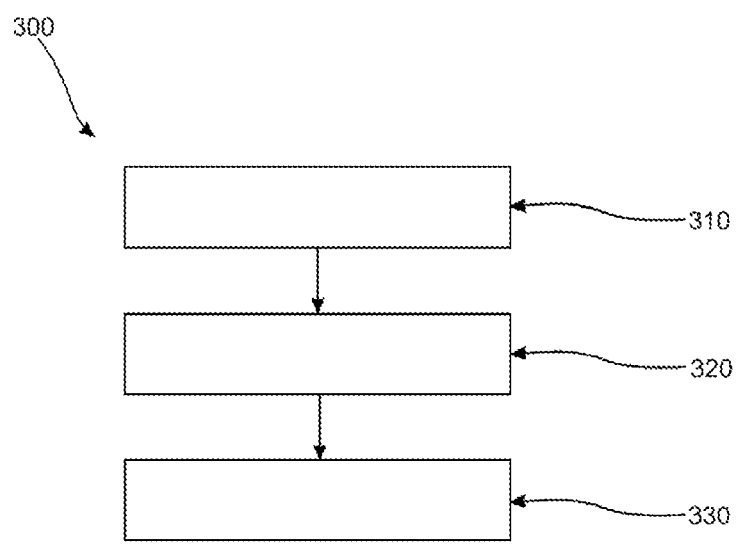

FIG. 3 shows a flow diagram of a method according to claim 1.

A lithotripsy apparatus 100 serves to carry out a method for determining an optimal frequency of an oscillating movement of a projectile excited by compressed air. The lithotripsy apparatus 100 can for example be a handheld device with a sonotrode attached to the distal end of the handheld device, wherein the sonotrode has a flexible waveguide shaft.

The lithotripsy apparatus 100 has a piezo element 130 arranged between a proximally arranged counter bearing 110 and a distally arranged horn 120. In this case, the piezo element 130 is mechanically coupled to the counter bearing 110 and to the horn 120. The piezo element 130 is subjected to an ultrasonic frequency of approx. 27 kHz by means of a signal generator, not illustrated.

The counter bearing 110 and the piezo element 130 each have a hollow-cylindrical shape. The horn 120 has a rotationally-symmetric shape with a cylindrical hollow along a central longitudinal axis. A proximal end of the horn 120 has the same outer diameter as the piezo element 130. Proceeding from the proximal end of the horn 120, the outer diameter of the horn initially remains constant for a predefined path and then decreases asymptotically to a value of the diameter, which is somewhat greater than the diameter of the cylindrical hollow in the interior of the horn 120.

The counter bearing 110 has in the present case the function of a reflector for the ultrasonic waves generated by the piezo element 130. The shape of the horn 120 and/or of the counter bearing 110 ensures that the transverse and rotational vibrations generated, just like the longitudinal vibrations generated, are guided optimally to a distal end of the sonotrode 170. It is advantageous here that the sonotrode 170 and the horn 120 consist of materials of substantially the same acoustic impedance.

In the interior 122 of the counter bearing 110 and of the horn 120 is located a hollow-cylindrical pipe section 140, the first end of which has, at a proximal end 112 of the counter bearing 110, a first stop 142 and the second end of which has, at a distal end 124 of the horn 120, a second stop 144.

A proximal end 146 of the pipe section 140 has a compressed air source 160 connected by means of a first valve 150. The first valve 150 has a check valve.

In the interior 122 of the pipe section 140 is arranged an elongated projectile 148, which can be accelerated by means of compressed air from the compressed air source 160 from the first stop 142 to the second stop 144. The projectile 148 can be slid freely back and forth in the pipe section 140. The projectile 148 can be accelerated from the second stop 144 to the first stop 142 by means of compressed air displaced by the projectile 148 and buffered in a storage chamber, not shown.

The projectile 148 has a cylindrical body made of very strong steel, which is slightly magnetic. At the proximal end 146 of the pipe section 140 is arranged a holding magnet not shown, which can draw in the projectile 148 and hold it there in the rest state.

A sonotrode 170 designed as a waveguide is arranged at a distal end 124 of the horn 120. In this case, a proximal end 172 of the sonotrode 170 is mechanically coupled to the second stop 144 such that an impact of the projectile 148 on the second stop 144 optimally transmits the impulse of the projectile 148 to the sonotrode 170. A diameter of the sonotrode 170 is smaller than a diameter of the pipe section 140.

In the case of pneumatic lithotripsy, both systems can be used, i.e. the ultrasound system with the ultrasound element 130 and the pneumatic system, in which the projectile 148 is accelerated by means of the compressed air from the compressed air source 160. This is called combined operation. Alternatively, the pneumatic system can also be operated without the ultrasound system. In the latter case, the entire system can be calibrated when the signal generator is switched off, i.e. the limit values of a current strength can be stored and used as a reference in the combined operation in which a measurement is more difficult since the ultrasonic frequency represents a source of interference.

In both cases, i.e. in the combined operation or if only the pneumatic system is operated, a power signal is measured by means of a current clamp not shown at a connection line between piezo element 130 and signal generator.

Since the ultrasonic vibrations of the piezo element 130 represent a source of interference, the power signal measured with the current clamp is frequency-filtered with an RLC circuit such that a small region around the ultrasonic frequency of approx. 27 kHz is filtered out of the power signal. The width of the filtered-out frequency is preferably adapted to the interference signal.

The frequency-filtered power signal is converted into an analogue rectified signal by means of a buffer circuit.

In the case of the rectified signal, two threshold values can be identified, a first threshold value corresponds to the projectile 148 impacting the first stop 142 and a second threshold value corresponds to the projectile impacting the second stop 144.

The rectified signal is recorded by a microcontroller, which controls and checks the entire evaluation. The microcontroller can carry out plausibility tests of the detected power signal in order to minimise incorrect measurements or measurement errors.

The method for determining a maximum or correspondingly optimal frequency of an oscillating movement of the projectile 148 excited by compressed air includes, according to a first step, repeatedly accelerating the projectile 148 by means of compressed air from the first proximal stop 142 of the pipe section 140 to a second distal stop 144 and from the second stop 144 to the first stop 140.

In this case, the first valve 150 is used to introduce compressed air into the pipe section 140 such that the projectile 148 is accelerated from the first stop 142 to the second stop 144, wherein the air displaced by the projectile 148 is buffered in a storage chamber and after the first valve 150 has been closed, the buffered compressed air is used to accelerate the projectile 148 from the second stop 144 to the first stop 142.

According to a second step of the method, the piezo element 130 is excited with an ultrasonic frequency. To this end, a signal generator operating at 27 kHz, not shown, is connected to the piezo element 130.

According to a third step of the method, a power signal of the piezo element 130 is detected caused by a tremor at the first stop 142 or the second stop 144 as a result of the projectile 148.

According to a fourth step of the method, the detected power signal is used to regulate the compressed air.

The power signal 180 has a plurality of exponentially decreasing sections modelled with a sine or cosine function, which are separated from one another in time. In this case, a first section 182 of the power signal 180 arises from a tremor of the projectile 148 at the second stop 144 and a second section 184 of the power signal 180 arises from a tremor at the first stop 142.

LIST OF REFERENCE NUMERALS

100 Lithotripsy apparatus
110 Counter bearing
112 Proximal end of the counter bearing
120 Horn
122 Interior of the counter bearing and of the horn
124 Distal end of the horn
130 Piezo element
140 Pipe section
142 First stop of the acceleration path
144 Second stop of the acceleration path
146 Proximal end of the acceleration path
148 Projectile
150 First valve
160 Compressed air source
170 Sonotrode
172 Proximal end of the sonotrode
180 Power signal
182 First section of the power signal
184 Second section of the power signal
300 Method
310 Method step
320 Method step
330 Method step

The invention claimed is:

1. A method for determining an optimal frequency of an oscillating movement of a force-accelerated projectile of an intracorporeal lithotripsy apparatus including the following steps:
repeatedly accelerating the projectile from a first stop of an acceleration path to a second stop, and from the second stop to the first stop, wherein a piezo element is arranged between a proximally arranged counter bearing and a distally arranged horn and is mechanically coupled to the counter bearing and to the horn, and the horn has a distally arranged sonotrode, wherein the acceleration path is arranged in the interior of the counter bearing and of the horn and the first stop is arranged at a distal end of the counter bearing and the second stop is arranged at a distal end of the horn,
detecting an electrical signal from the piezo element caused by a tremor at the first stop and/or the second stop as a result of the projectile; and
using the detected electrical signal to control a medium which generates the force and which is used to accelerate the projectile from the first stop of the acceleration path to the second stop, and from the second stop to the first stop.

2. The method according to claim 1, characterised in that the projectile is accelerated by means of compressed air, by means of an electromechanically imparted force or by means of a mechanical apparatus and/or in that the medium is compressed air, an electromagnetic field or a mechanical apparatus.

3. The method according to claim 1, further comprising:
exciting the piezo element with an ultrasonic frequency.

4. The method according to claim 1, characterised in that the acceleration path is implemented with a pipe section, wherein a first end of the pipe section has the first stop and a second end of the pipe section has the second stop.

5. The method according to claim 4, characterised in that a first valve is used to introduce compressed air into the pipe section such that the projectile is accelerated from the first stop to the second stop, wherein the air displaced by the projectile is buffered in a storage chamber and after the first valve has been closed, the buffered compressed air is used to accelerate the projectile from the second stop to the first stop.

6. The method according to claim 5, characterised in that the electrical signal of the piezo element is a power signal, which is measured by means of a coil.

7. The method according to claim 1, further comprising:
frequency-filtering the power signal measured at the piezo element and
rectifying the frequency-filtered power signal.

8. The method according to claim 7, further comprising:
identifying at least one threshold value of the rectified frequency-filtered power signal, which corresponds to the projectile impacting the first stop or second stop.

9. A lithotripsy apparatus, in particular for carrying out a method according to claim 1, comprising:
a piezo element arranged between a proximally arranged counter bearing and a distally arranged horn, wherein the piezo element is mechanically coupled to the counter bearing and to the horn, and a hollow-cylindrical acceleration path is arranged in the interior of the counter bearing and of the horn, said hollow-cylindrical acceleration path having, at a proximal end of the counter bearing, a first stop and, at a distal end of the horn, a second stop, wherein a proximal end of the acceleration path has a compressed air source connected by means of a first valve or the lithotripsy apparatus has an apparatus for generating an electromagnetic field to apply a force imparted electromagnetically on a projectile; and the projectile is arranged in the interior of the acceleration path, said projectile being designed and configured to be accelerated by means of compressed air from the compressed air source, or the electromagnetically imparted force from the first stop to the second stop and to be accelerated by means of compressed air displaced by the projectile and buffered in a storage chamber, or the electromagnetically imparted force from the second stop to the first stop,
a sonotrode, which is designed as a waveguide and which is arranged at a distal end of the horn, wherein a proximal end of the sonotrode is mechanically coupled to the second stop and the lithotripsy apparatus is designed and configured such that an electrical signal from the piezo element causing a tremor at the first stop and/or second stop as a result of the projectile, can be detected and is used for controlling the compressed air from the compressed air source or for controlling the electromagnetically imparted force.

* * * * *